United States Patent [19]
Durfor et al.

[11] Patent Number: 5,314,642
[45] Date of Patent: May 24, 1994

[54] INTERACTION SYSTEM COMPRISING A SURFACTANT-STABILIZED AQUEOUS PHASE CONTAINING AN ANTIBODY FRAGMENT

[75] Inventors: Charles N. Durfor, Rockville, Md.; Richard J. Bolin, Fairfax; Allen R. Schantz, II, Reston, both of Va.; Richard J. Massey, Rockville, Md.

[73] Assignee: IGEN, Inc., Rockville, Md.

[21] Appl. No.: 938,489

[22] Filed: Aug. 31, 1992

Related U.S. Application Data

[63] Continuation of Ser. No. 188,251, Apr. 29, 1988, abandoned, and a continuation-in-part of Ser. No. 674,253, Nov. 27, 1984, Pat. No. 4,888,281.

[51] Int. Cl.$^5$ .............................................. B01J 13/00
[52] U.S. Cl. ..................................... 252/309; 435/68.1; 435/177; 436/512; 436/535; 436/548; 436/829; 436/513
[58] Field of Search ............... 435/810; 252/308, 309; 436/512, 513, 535, 548, 826, 829; 530/387.1, 388.1, 412, 418, 420

[56] References Cited

U.S. PATENT DOCUMENTS

| | | | |
|---|---|---|---|
| 3,654,090 | 4/1972 | Schuurs et al. | 435/7.93 |
| 4,438,052 | 3/1984 | Weder et al. | 424/450 X |
| 4,582,731 | 4/1986 | Smith | 427/421 |
| 4,640,898 | 2/1987 | Halfman | 436/829 X |
| 4,728,575 | 3/1988 | Gamble et al. | 424/1.1 X |
| 5,151,266 | 9/1992 | Morgan, Jr. et al. | 424/85.8 |
| 5,156,965 | 10/1992 | Schochetman et al. | 530/388.1 X |
| 5,158,704 | 10/1992 | Fulton et al. | 252/309 |
| 5,229,272 | 7/1993 | Paul et al. | 435/68.1 |
| 5,236,825 | 8/1993 | Iverson et al. | 435/68.1 |

FOREIGN PATENT DOCUMENTS

| | | |
|---|---|---|
| 0160552 | 11/1985 | European Pat. Off. |
| 02414 | 6/1985 | PCT Int'l Appl. |
| 85/02414 | 6/1985 | PCT Int'l Appl. |
| WO86/04065 | 7/1986 | PCT Int'l Appl. |
| WO87/02250 | 4/1987 | PCT Int'l Appl. |
| 1445968 | 8/1976 | United Kingdom |

OTHER PUBLICATIONS

*Bioorg Khim.*, vol. 12, No. 5, issued 1986, A. N. Eryomin, p. 612.

*Angewandte Chemie*, vol. 24, No. 6, issued Jun. 1985, P. L. Luisi, pp. 441–448.

L. S. Kaminsky and A. J. Davidson, *FEBS Letters* 3, 338, (1969).

A. A. Klyosov, N. Van Viet, and I. V. Berezin, *Eur. J. Biochem.*, 59, 3, (1975).

F. A. Bettelheim and A. Lukton, *Nature* 198, 357 (1963).

(a) C. Gitler and M. Montal, *Biochem and Biophys Res. Comm.* 47, 1486 (1972); (b) *FEBS Letters* 28, 329 (1972).

K. Martinek, A. V. Levashoft, N. L. Klyachko, and I. V. Berezin, *Doklad Ada Nauk USSR* (Engl. edit.), 236, 951 (1978).

P. L. Luisi, F. J. Bonner, A. Pellegrini, P. Wiget, and R. Wolf, *Helv. Chim. Acta* 62, 740 (1979).

J. S. Huang and M. W. Kim, *Phys. Rev. Lett.* 47, 1462 (1981).

M. Kotlarchyk, S.-H. Chen, J. S. Haung, and M. W. Kim, *Phys. Rev. A* 29, 2054 (1984).

A. De Marco, E. Menegatti, and P. L. Luisi, *J. Biochem and Biophys. Meth.* 12, 325 (1986).

(List continued on next page.)

Primary Examiner—Robert L. Stoll
Assistant Examiner—John M. Covert
Attorney, Agent, or Firm—Curtis Morris & Safford

[57] ABSTRACT

An interaction system, including an antibody or, antibody fragment having functional capability, which comprises a surfactant-stabilized microheterogeneous dispersion of aqueous phase in a water-immiscible medium, said aqueous phase containing an amount of said antibody or said fragment in a functional state sufficient to effect the interaction; and methods for making and for using said system.

40 Claims, 5 Drawing Sheets

OTHER PUBLICATIONS

P. L. Luisi, *Angew Chem. Int. Ed. Engl.* 24, 439 (1985).
K. Larsson, P. Adlecreutz, and B. Mattiasson, "Biocatalysis in Organic Media", C. Laane, J. Tramper, and M. D. Lilly, Eds. Elsevier Science Publishers B. V., Amsterdam, p. 355 (1986).
P. L. Luisi, P. Luthi, I. Tomka, J. Prenosil, and A. Pande, *Annals N.Y. Acad. of Sci.* 434, 549 (1984).
D. Han and J. S. Rhee, *Biotech. and Bioeng.* 28, 1250 (1986).
M. A. Hernandez-Torres, J. S. Landy, and J. G. Dorsey, *Anal. Chem.* 58, 744 (1986).
R. W. Gale, J. L. Fulton, and R. D. Smith, *Anal. Chem.* 59, 1977 (1987).
K. E. Goklen and T. Alan Hatton, *Biotech Progress* 1, 69, (1985).
L. J. Karr, S. G. Shafer, J. M. Harris, J. M. Van Alstine, and R. S. Snyder, *J. Chromatography* 354, 269 (1986).
A. N. Eremin, M. I. Savenkova, and D. I. Metelitsa, *Bioorg. Khim.* 12, 606 (1986) translation.
K. Martinek, et al., *Science,* 218, 889–891 (1982).
Johnstone et al., *Biocatalysis in Organic Media,* 387–392 (1987).
Klyachko, et al., *Institute of Organic Chemistry and Biochemistry,* 149–154 (1986).
Berezin, et al., Annals N. Y. *Academy of Sciences,* 577–579.
Nakanishi, et al., *Eur. J. Biochem.* 161, 533–540 (1986).
Nakanishi, et al., *Eur. J. Biochem.* 161, 541–549 (1986).
Whitesides, *Enzymes in Organic Synthesis,* 76–96 (1985).
Klibanov, et al., *Protein Immobilization on Liposomes,* 580–581.
Duarte, et al., *Annals N. Y. Academy of Sciences,* 573–576.
Boutelje, et al., Biocatalysis in Organic Media, 361–368.
Leong, et al., *The Journal of Physical Chemistry,* 86, 13, (1982).
Luthi, et al., *J. Am. Chem. Soc.,* 106, 1285–1286 (1984).
Lasic, et al., *J. Am. Chem. Soc.,* 110, 970–971 (1988).
Tran, *Annal. Chem.,* 60, 182–185 (1988).
Armstrong, et al., *Annal. Chem.,* 60, 86–88 (1988).
Mayer, et al., *Biochemistry,* 27, 2053–2060 (1988).
Breslow, et al., *Tetrahedron Letters,* 29, No. 14, 1635–1638 (1988).
Hilvert, et al., *J. Am. Chem. Soc.,* 107, 5805–5806 (1985).
Dekker, et al., *Biocatalysis in Organic Media,* 285–288 (1987).
Kahlweit, *Science,* 240, 617–621 (1988).
Erhan, S. and Greller, L. D., *Nature,* vol. 251 353 (1974).
Chemical Abstracts, vol. 107, Abstract No. 114174t.

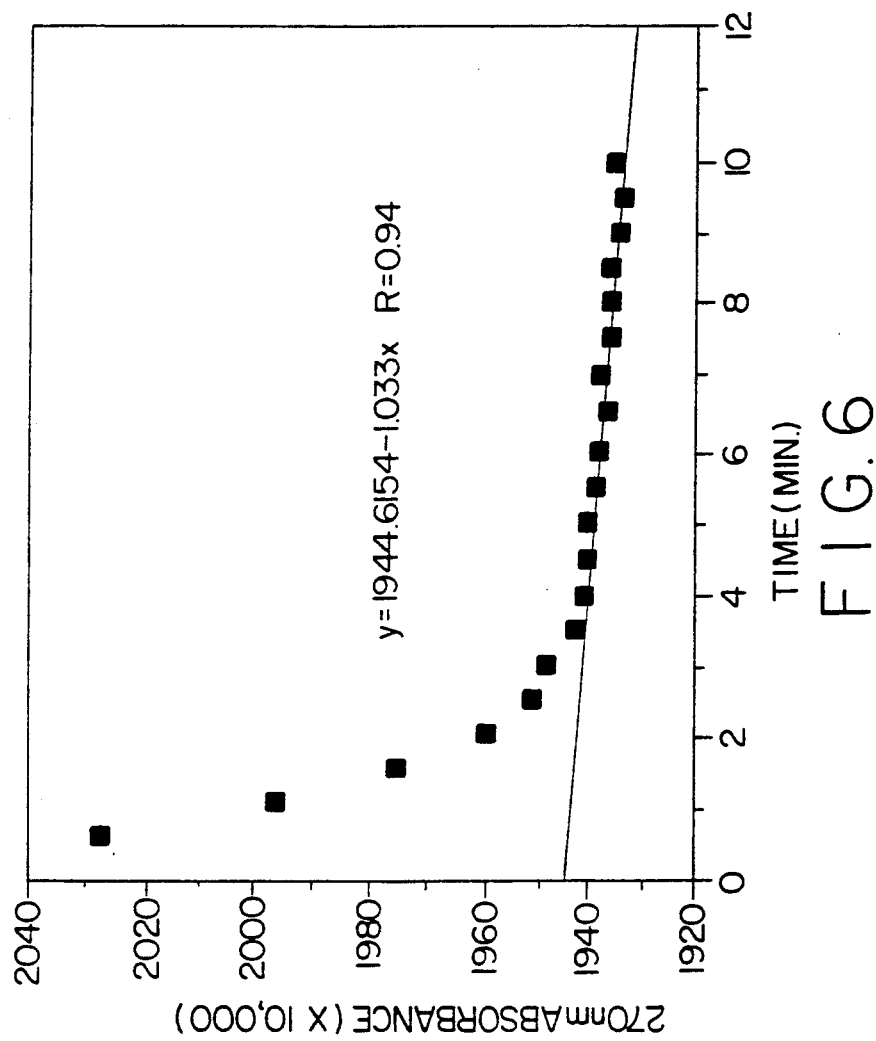

INTERACTION SYSTEM COMPRISING A SURFACTANT-STABILIZED AQUEOUS PHASE CONTAINING AN ANTIBODY FRAGMENT

This application is continuation of application Ser. No. 07/188,251, filed Apr. 29, 1988, now abandoned, and is a continuation-in-part of copending U.S. patent application Ser. No. 06/674,253, filed Nov. 27, 1984, now U.S. Pat. No. 4,888,281.

FIELD OF THE INVENTION

The present invention relates to a system comprising a surfactant-stabilized disperse aqueous phase containing an antibody or antibody fragment in a functional state, and to methods for making such systems as well as to methods of utilizing such systems.

BACKGROUND OF THE INVENTION

While living systems are often viewed as the reaction of biochemicals in water, considerable research has been devoted to the study of the structure and function of biochemicals in mixed water-organic solvent systems. In 1969, Kaminsky and Davidson (1) (see bibliography concluding this section for citations to referenced publications) examined the effects of organic solvents on the low molecular weight protein cytochrome c (12K daltons). A similar approach was used by A.A. Klyosov et al. (2) and Bettelheim and Lukton (3) to measure the enzymatic activity of small molecular weight proteins.

Gitler and Montal (4) radically departed from these early studies in their stabilization of cytochrome c in a solvent system composed primarily (90%) of a water-immiscible solvent, decane, by complexation with a biological detergent, i.e., phospholipids. Marinek et al. (5) explored the stabilization and subsequent enzymatic activity of another low molecular weight protein, chymotrypsin (22K daltons), in iso-octane. The anionic detergent used by Marinek et al. was a non-biological mimic of phospholipids, namely sodium bis-(2-ethylhexyl)-sulfosuccinate ("AOT"). Similarly, Luisi et al. (6) found that chymotrypsin, and other low molecular weight enzymes, trypsin and pepsin (23K and 35K daltons, respectively), retained their enzymatic activity in the water-immiscible solvent cyclohexane when complexed with the cationic detergent methyltrioctylammonium chloride. Luisi et al. suggested that those enzymes retained their basic natural structure within a small aqueous core surrounded by a sphere of detergent and organic solvent. Such structures were termed "reverse micelles", forming within water-immiscible solvents when detergent content is above the critical micelle concentration ("CRC") and when the molar ratio of water to detergent ("$W_o$") is in the range from 5:1 to 50:1, inclusive. The bulk of these solutions (80–90%) is composed of a water-immiscible organic solvent.

Physical evidence tending to confirm the existence of reverse micelles has been gained from quasi-elastic light scattering, Huang and Kim (7), and small-angle neutron scattering measurements, M. Kotlarchyk et al. (8). Structural and mechanistic information concerning proteins within reverse micelles has been obtained through NMR (DeMarco et al. (9)), ultraviolet, circular dichroism and fluorescence (P.L. Luisi, 1979 (6)) spectroscopies, as well as enzymatic kinetic analyses.

A variety of low molecular weight proteins and enzymes have been stabilized in a variety of solvents and with a variety of surfactant and co-surfactant systems (P.L. Luisi, 1985 (10)). Although a diverse set of conditions was used in these experiments, some conclusions can be drawn. First, these studies were largely performed with relatively low molecular weight proteins (e.g., cytochrome c (12K daltons), ribonuclease (13K daltons), lysozyme (14K daltons), chymotrypsin (23K daltons), trypsin (35K daltons), alcohol dehydrogenase (37K daltons), rhodopsin (38K daltons), and lipase (45K daltons)), when compared to the molecular weight of the immunoglobulin molecules (150K daltons). Second, the majority of these proteins displays maximal catalytic activity at a water-to-detergent ratio ($W_o$) of about 10–15. (We note that lipase of 100K daltons has been reported, and that this enzyme has been said to have an activity which increases up to $W_o$ of about 30 and then levels off with (Luisi et al. (12)); however, the molecular weight of this enzyme is significantly less than that of an antibody as contemplated by the present invention, and further the enzyme is lipophilic rather than hydrophilic, and thus its behavior should not be viewed as indicative of antibody behavior. And finally, as suggested by P.L. Luisi et al. (6), "Another interesting property of the phase transfer process . . . is its selectivity towards certain proteins" (p. 751). Factors such as protein size and charge, solution pH, surfactant composition and concentration as well as ionic strength, determine if a particular type of protein can be successfully stabilized within reverse micelles. Particular combinations of these factors are specific to different types of proteins, and this undercuts the predictability of whether one protein type can be stabilized from the finding that a different protein type can. Accordingly, it would not have logically followed that the teachings of the aforementioned workers could be extrapolated beyond the specific conditions and materials utilized by them.

It is also important to note that while stabilization of enzymes within water/water-immiscible biphasic systems was explored to catalyze reactions with water-insoluble substrates (Larsson (11); P.L. Luisi et al. (12)), or for mimicking physiological conditions (Han and Rhee (13)), there are other applications of reverse micelles such as both liquid and HPLC chromatography (M.A. Herandez, 1986 (14)), with supercritical fluids (R.W. Gale et al., 1987 (15)) and in protein extraction (Goklen and Hatton, 1985 (16)).

However, reports of antibody stabilization in these water-immiscible solvents (both organic liquids and supercritical fluids) are extremely limited.

Karr et al. (17) examined a covalent modification of IgG molecules with polyethylene glycol (PEG) as a method of improving the solubility of antibodies in a dextran phase of a biphasic solution. While a dextran phase is far more water-miscible than iso-octane or benzene, the major drawback of this approach is the extra time-consuming steps required for forming the PEG-antibody covalent complex and the possibility that chemical modification of a protein with PEG could also covalently modify amino acid residues in the antigen binding site, thereby reducing the antibody's antigen-binding capacity. In addition, there is no guarantee that this technique works with water-immiscible solvents.

Eremin et al. (18) examined the effects of antibodies directed against horseradish peroxidase in 50 mM aqueous AOT solutions in heptane. The thrust of this work was to study the loss of peroxidase activity observed due to mixing of enzyme and polyclonal anti-peroxidase antibodies. But there is no indication that the antibody was of a monoclonal nature or had a molecular weight which would have been conducive to solubilization in the reverse micelles at the conditions utilized, that the enzyme was inactivated by the antibody, or even that the system of Eremin et al. contained an effective amount of antibody in a functional state. Significantly, no attempt was made to test the antibody's antigen-binding capability in an ELISA analysis after solubilization in iso-octane. Since the presence of large antibodies in the polyclonal mixture, such as those of the IgM nature (970K daltons), could well have caused the applied conditions to be unfavorable for solubilization of antibodies or horseradish peroxidase, this article would not have disclosed use of an effective amount of functional antibodies in an aqueous/non-aqueous biphasic system to the skilled worker.

The development of information concerning conditions for stabilizing an effective amount of antibody or antibody fragment in a heterogeneous system comprising a dispersed aqueous phase, with retention of an effective amount of antibody or antibody fragment in a functional state, would be a significant step forward in the art.

(1) L.S. Kaminsky and A.J. Davidson, *FEBS Letters* 3, 338 (1969).
(2) A.A. Klyosov, N. Van Viet, and I.V. Berezin, *Eur. J. Biochem.* 59, 3 (1975).
(3) F.A. Bettelheim and A. Lukton, *Nature* 198, 357 (1963).
(4) (a) C. Gitler and M. Montal, *Biochem and Biophys Res. Comm.* 47, 1486 (1972); (b) *FEBS Ietters* 28, 329 (1972).
(5) K. Martinek, A.V. Levashoft, N.L. Klyachko, and I.V. Berezin, *Doklad Ada Nauk SSSR* (Engl. edit), 236, 951 (1978).
(6) P.L. Luisi, F.J. Bonner, A. Pellegrini, P. Wiget, and R. Wolf, *Helv. Chim. Acta* 62, 740 (1979).
(7) J.S. Huang and M.W. Kim, *Phys. Rev. Lett.* 47, 1462 (1981).
(8) M. Kotlarchyk, S.-H Chen, J.S. Huang, and M.W. Kim, *Phys. Rev. A* 29, 2054 (1984).
(9) A. De Marco, E. Menegatti, and P.L. Luisi, *J. Biochem and Biphys Meth.* 12, 325 (1986).
(10) P.L. Luisi, *Angew Chem Int Ed Engl.* 24, 439 (1985).
(11) K. Larsson, P. Adlecreutz, and B. Mattiasson, "Biocatalysis in Organic Media," C. Laane, J. Tramper, and M.D. Lilly, Eds., Elsevier Science Publishers B.V., Amsterdam, p. 355 (1986).
(12) P.L. Luisi, P. Luthi, I. Tomka, J. Prenosil, and A. Pande, *Annals N.Y. Acad. of Sci.* 434, 549 (1984).
(13) D. Han and J.S. Rhee, *Biotech and Bioeng* 28, 1250 (1986).
(14) M.A. Hernandez-Torres, J.S. Landy, and J.G. Dorsey, *Anal. Chem.* 58, 744 (1986).
(15) R.W. Gale, J.L. Fulton, and R.D. Smith, *Anal Cheml* 59, 1977 (1987).
(16) K.E. Goklen and T. Alan Hatton, *Biotech Progress* 1, 69, (1985).
(17) L.J. Karr, S.G. Shafer, J.M. Harris, J.M. Van Alstine, and R.S. Snyder, *J. Chromatography* 354, 269 (1986).
(18) A.N. Eryomin, M.I. Savenkova, and D.I. Metelitsa, *Bioorg. Khim* 12, 606 (1986).

OBJECTS OF THE INVENTION

It is an object of this invention to provide a system for interacting an antibody or fragment thereof with one or more other species of interest.

It is another object of the present invention to provide stabilized antibodies or antibody fragments contained in a system comprising a microheterogeneously dispersed aqueous phase.

It is yet another object of the present invention to provide a system in which an antibody or fragment thereof having a catalytic functionality is made available for the conversion of one or more reactants into one or more desired products.

It is a further object of this invention to increase the acceleration factor for catalysis by an antibody or antibody fragment (i.e., the rate constant of an antibody-catalyzed reaction divided by the rate constant of the uncatalyzed reaction in solvent (background hydrolysis) in which the one or more reactants are contained).

It is a still further object of the present invention to provide catalysis by an antibody or fragment thereof in a system comprising a microheterogeneously dispersed aqueous phase for which there is no existing enzyme or man-made catalyst.

It is another object of the present invention to provide a highly sensitive antibody-containing antibody-fragment-containing system having an enhanced capability to detect one or more species of interest in a water-immiscible medium.

It is yet another object of the present invention to provide an antibody-containing or antibody-fragment-containing system well-suited for the isolation of protein or non-protein materials.

It is also a further object of this invention to provide a method for making a system in which one or more of the objectives set forth above can be achieved, and a method for utilizing such a system.

SUMMARY OF THE INVENTION

The foregoing and other objects are met by the present invention as set forth herein.

In one aspect, the invention is an interaction system including an antibody, or a fragment thereof having functional capability, which comprises a surfactant-stabilized microheterogeneous dispersion of aqueous phase in a water-immiscible medium, said aqueous phase containing an amount of said antibody or fragment in a functional state sufficient to effect the interaction.

In another aspect, the present invention is, in a water-immiscible medium, an interaction system including an antibody, or a fragment thereof having functional capability, which comprises a plurality of surfactant-stabilized microheterogeneously disperse aqueous phase particles, said particles containing an amount of said antibody or fragment in a functional state sufficient to effect said interaction.

In yet another aspect, the invention is a method of forming an interaction system including an antibody, or a fragment thereof having functional capability, which comprises surfactant-stabilizing a microheterogeneous dispersion of aqueous phase in a water-immiscible medium, said aqueous phase containing an amount of said antibody or fragment in a functional state sufficient to effect the interaction.

In still another of its aspects, the present invention is a method of interacting an antibody, or a fragment thereof having functional capability, with at least one species, which comprises maintaining a system comprising a surfactant-stabilized microheterogeneous dispersion of aqueous phase in a water-immiscible medium, said aqueous phase containing an amount of said antibody or fragment in a functional state under which the antibody or fragment is accessible to said species, and that are sufficient to effect said interaction, at conditions sufficient to effect said interaction for a time sufficient for said interaction to occur.

And, in a still further aspect, the present invention is a method of interacting an antibody, or a fragment thereof having functional capability, with at least one species, which comprises maintaining said antibody in a plurality of surfactant-stabilized microheterogeneously dispersed aqueous phase particles, said aqueous phase particles containing an amount of said antibody or fragment in a functional state sufficient to effect said interaction, at conditions under which the antibody or fragment is accessible to said species, and that are sufficient to effect said interaction, for a time sufficient for said interaction to occur.

Practice of the present invention affords many advantages. A stabilized system for interacting an antibody, or fragment thereof as aforesaid, with one or more species of interest is provided; the antibody component is maintained in a functional state and is therefore readily available for interaction with the species (e.g. antigens, or haptens, substrates or reactants). Also, the invention provides a reliable, viable catalytic antibody (or catalytic antibody fragment) system, especially one in which the interaction of the catalyst with one or more lipophilic reactants or products is achieved. This makes possible the catalysis of interactions in an aqueous/non-aqueous biphasic solvent system for which enzymatic or other man-made catalysts are not available. Additionally, by taking advantage of the antibody's (or fragment's) greater affinity toward one reactant relative to another reactant or to a product, or the relatively greater solubility of a reactant in the microheterogeneously disperse aqueous phase as compared to the solubility of that reactant under bulk aqueous conditions, or the relatively greater solubility in the water-immiscible medium of a reactant or product vis-a-vis another reactant, a catalytic antibody (or catalytic antibody fragment) system can be utilized to control the effective concentration of respective reactants and products in the vicinity of the catalyst. This offers an elegant means for minimizing reaction rate-limiting effects. Further, since the microheterogeneously dispersed aqueous phase has different thermodynamic properties than bulk aqueous phases, interactions with the antibody (or fragment thereof as aforesaid) which could not be feasibly carried out in a bulk aqueous material (for instance, an interaction which is only favored at well below 0° C., the freezing point of water) can be performed successfully with the invention (because the freezing point of the microheterogeneous disperse aqueous phase is so much lower than 0° C. that the reaction can proceed). Moreover, with the practice of the invention, the overall rate constant acceleration of catalysis with an antibody or appropriate fragment thereof is increased by reducing or effectively eliminating undesirable solvent-catalyzed background background reaction. This can be critical to a synthesis if the catalyzed reaction (such as a reaction producing one of a pair of stereoisomers) normally proceeds simultaneously with a non-stereospecific background reaction (that is, a reaction producing a racemic mixture), because in the absence of the background reaction the pure isomer desired is obtained. Additionally, the invention provides a high capability system for detecting antigens or haptens or substrates which are insoluble, or only sparingly soluble, in water by complexing them with antibodies or fragments residing in the aqueous portion of a system comprising a microheterogeneous disperse aqueous phase. Also, the invention provides a reliable, highly-effective system for isolation of protein and non-protein species.

Thus, the invention has utility in analytical, synthetic, separation and therapeutic applications. Its versatility and adaptability make evident its significance as a step forward in the art.

BRIEF DESCRIPTION OF THE DRAWINGS

FIG. 6 is a curve showing results of the hydrolysis reaction with a similar 20-G9 antibody solution in the microemulsion phase inhibited by transition state analog inhibitor.

DESCRIPTION OF CERTAIN PREFERRED EMBODIMENTS

Figure 1:
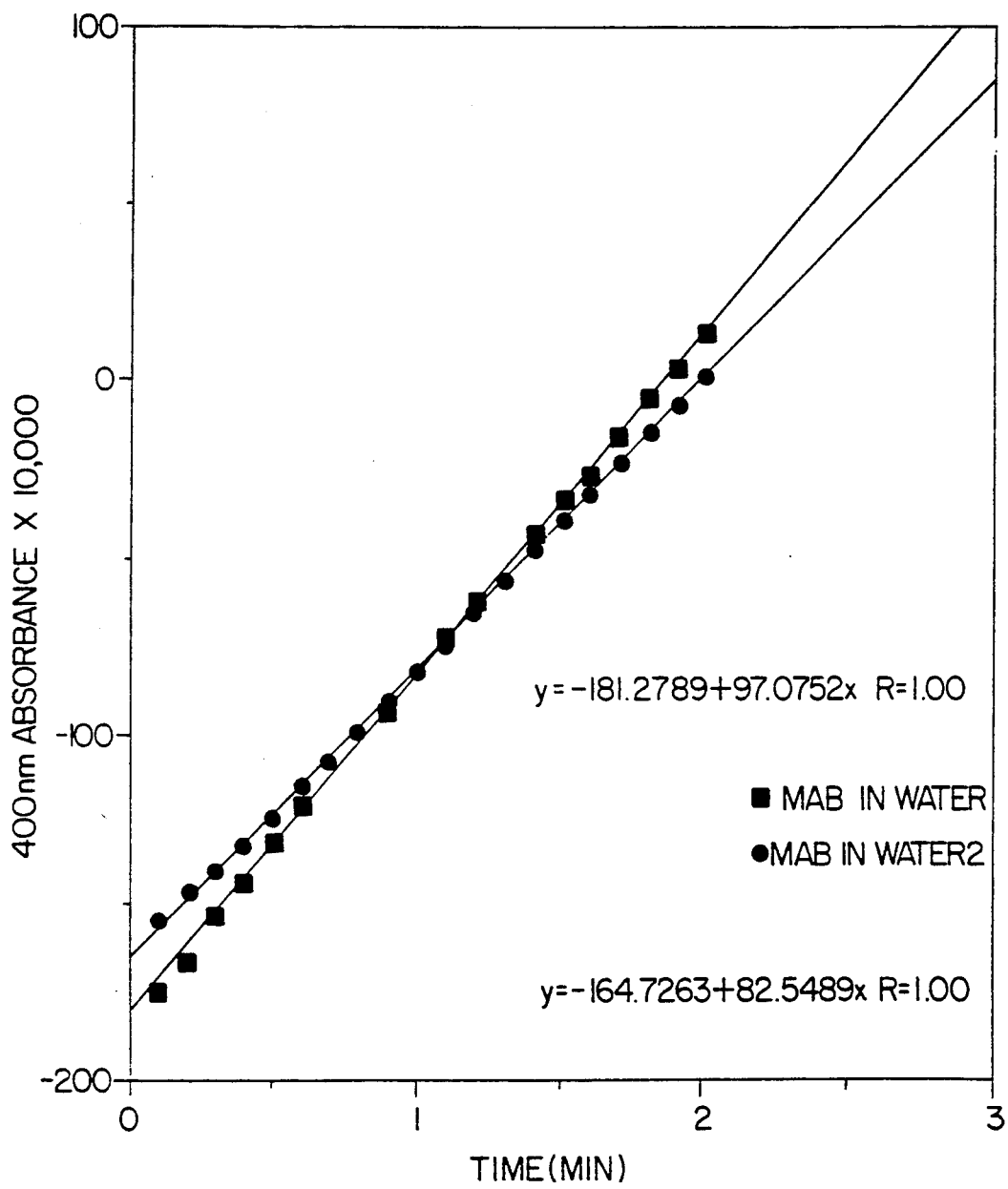
FIG. 1 is a set of curves showing progression of a hydrolysis reaction catalyzed with 48-G7 antibody in aqueous solution in accordance with the invention.

It is important that the antibody, or antibody fragment having functional capability, contained in the aqueous phase be capable of interacting with species of interest normally contained in the water-immiscible medium. This makes feasible an interaction between an antibody or fragment, which is hydrophilic, and one or more lipophilic species contained in the water-immiscible medium, even when such species are insoluble or only sparingly soluble in water—a reaction which would not be feasible if the antibody or fragment were in a bulk aqueous phase. As explained below, practice of the present invention provides a manner in which the antibody (or antibody fragment) and species of interest can be interacted in a medium which accommodates both for at least the time necessary for the desired interaction to occur.

As pertains to the present invention, the anti( body's or fragment's function is to bind with specific preselected molecules, either temporarily or permanently. (The antibody fragment is a portion of the antibody whole, which portion is capable of binding with a molecule of interest on its own, without the balance of the antibody; thus, the fragment's functional capability is the capability to bind with a species of interest.) This is the essential nature and definition of the antibody's or fragment's being in a functional state. When the antibody or fragment is in a denatured state, it has lost its binding affinity. This can occur when the antibody or fragment is exposed to a contaminant, such as an organic liquid, which adversely affects the antibody or fragment by causing it to lose its native conformation, and thus its ability to bind to the species of interest. Thus, to be maintained in a functional state the antibody or fragment is solubilized in water.

This behavior presents a significant dilemma, namely, how to introduce the antibody or fragment into a water-immiscible environment for reaction with hydrophobic species contained therein while still protecting the antibody or fragment from contaminants which would denature it. The present invention's elegance is in the resolution of that dilemma. An antibody or fragment is maintained in a functional state by surrounding it with an aqueous shield which protects it against contact with substances that would denature it and yet provides a medium with which both the hydrophilic antibody or fragment and lipophilic species are compatible—at least for the time necessary to effect the desired interaction.

The essence of the invention is the formation of a microheterogeneously disperse aqueous phase, particles of which contain antibody, or antibody fragment having functional capability, stabilized by the action of a surfactant. The aqueous phase is typically in microemulsion form, or present as a plurality of reverse micelles. However, a microheterogeneous dispersion of the aqueous phase is not limited to either a microemulsion or reverse micelle formation, but encompasses any embodiment in which the aqueous phase particles are of appropriate mass so that, when stabilized (as further explained hereinafter), the properties of that phase render it suitable for containing the antibody or fragment thereof, for temporarily accommodating species which are insoluble or only sparingly soluble in water, and for permitting diffusion of such species as desired across the aqueous phase/water-immiscible medium boundary at an acceptably high rate. In general, the water pools of the aqueous phase particles are not of such large mass that they exhibit bulk properties incompatible with the present invention's practice. On the other hand, they are not of such small mass that they cannot be surfactant-stabilized so as to be capable of containing the antibody or antibody fragment, not to mention the complex or conjugate of the antibody (or fragment) and species of interest. When a suitable water:surfactant ratio ($W_o$) is used, the properties of the constituent water of the aqueous phase particles differ favorably from those of a bulk aqueous mass—for example, in their increased capacity to protect the antibody or antibody—fragment while accommodating species not appreciably soluble in the bulk mass, and in their lower freezing points.

The microheterogeneously dispersed aqueous phase particles are usually smaller in maximum dimension when unoccupied than if they contain an antibody or antibody fragment, or its complex or conjugate with one or more species with which the antibody or fragment is to interact. It is a special advantage of using properly surfactant-stabilized microheterogeneously dispersed aqueous phase particles that, despite their much smaller size than the antibody (or fragment) and the above-mentioned complex or conjugate, the particles are sufficiently "elastic" that they can expand to envelope the antibody, antibody fragment, complex or conjugate. For example, a typical surfactant-stabilized reverse micelle is spheroidal and of a size approximately 10 nanometers in its maximum dimension when it does not contain an antibody, antibody fragment complex or conjugate. But, when stabilized in accordance with the present invention, the micelle can accommodate an antibody or fragment of size much greater then the unoccupied micelle. This is accomplished by providing sufficient water in the micelle so that it can surround the antibody or fragment and conform to its configuration. This provides an aqueous exterior shield protecting the antibody or fragment from contact with denaturing substances, and at the same time presenting a medium in which interaction between an antibody (or fragment) and one or more species of interest can be conducted. It can be seen that the size of an antibody, antibody fragment, complex or conjugate as aforesaid will ordinarily determine the size of the aqueous particle in which the antibody, fragment, complex or conjugate is contained. Indeed, the microheterogeneous dispersion of aqueous phase is so fine that light can typically be passed through the dispersion in a water-immiscible medium because—even when the aqueous phase particles are occupied by an antibody, antibody fragment, complex or conjugate—their maximum dimension is less than the wavelength of visible light, which is approximately 350–400 nanometers. Thus, the microheterogeneous dispersion mimics a solution of the antibody or antibody fragment in a water-immiscible medium even to the extent of being transparent.

A further benefit of practicing the invention is that solubilizing the antibody or antibody fragment in microheterogeneously disperse aqueous phase particles these aqueous phase particles are typically liquid particles in a water-immiscible medium minimizes background interaction in the medium. This is especially helpful when the interaction is a reaction in which making of the desired product(s) is normally accompanied by undesirable by-products resulting from background reaction such as when the desired reaction yields only a single specific isomer, but the background reaction produces a racemic mixture of two isomers. Catalysis by an antibody or antibody fragment according to the invention which effectively eliminates background reaction yields a pure isomer as desired. The invention's conferring of this benefit is confirmed in one of the examples set forth hereinafter.

The concentration of the antibody or fragment in the aqueous phase is at least that giving an amount of antibody or fragment in a functional state sufficient to effect the desired interaction. Due to the special properties of the microheterogeneously dispersed aqueous phase particles, the antibody or fragment can be contained in the aqueous phase/fluid system in large amounts, e.g. up to and including 2g/ml of fluid. In certain embodiments, use of a lesser amount of antibody or fragment, for instance, 30–50 μg/ml of fluid suffices.

In solubilizing an antibody or fragment thereof, it is often advantageous to add to the aqueous phase at least one buffering compound, such as a phosphate buffer, to give it a desired pH. This is to maintain conditions which are conducive to solubilization of the antibody or fragment in an aqueous phase and/or which favor the driving of the desired interaction to completion. Examples of additional suitable buffering compounds are imidazole, borate, or tris buffer. The compound is selected in light of the pH which is desired for the aqueous phase. The pH is typically in a range from 4–11, preferably 5–10, especially 6–10.

Once equipped with the teachings herein, it will be well within the skill of the art to determine empirically the amount of antibody or antibody fragment which is most advantageously utilized, and the pH of the aqueous phase in which the antibody or antibody fragment is solubilized, without undue experimentation.

The water-immiscible medium is, generally speaking, a water-immiscible fluid or a water-immiscible supercritical fluid. The particular water-immiscible medium employed is chosen (where applicable) for its ability to solubilize one or more species to be interacted with the antibody or antibody fragment, and/or (if applicable) any product to which one or more of such species are converted. Another factor which governs the choice of the water-immiscible medium is the temperature range of interest.

Typically, the water-immiscible fluid is an organic liquid, or a mixture of organic liquids, which are not miscible with water. Examples of such liquids are aromatics and substituted aromatics such as benzene, toluene, xylene, ethylbenzene, propylbenzene, chlorobenzene, biphenyl, and diphenylmethene, alkanes and substituted alkanes such as n-pentane, n-hexane, cyclohexane, n-heptane, iso-octane, decane, trichloromethane, dichloromethane and trichloroethane, and ethers such as diisopropyl ether and ethyl ether, as well as sparingly water-soluble substances such as acetone and dioxane. However, any organic solvent will do, so long as it is water-immiscible (i.e., it is at most sparingly soluble in water, and thus is suitable for formation of the desired microheterogeneous dispersion of the aqueous phase) and (if applicable) it solubilizes the species to be reacted with the antibody or antibody fragment in the aqueous phase, and/or any products which are produced, that the practitioner desires be solubilized.

It is also suitable, in certain embodiments of the invention, to use a water-immiscible fluid which is not in liquid form per se. An example of such a fluid would be a fog composed of droplets each made of an organic liquid, for instance benzene, surrounding an aqueous phase droplet containing an antibody or antibody fragment, with the benzene-enveloped aqueous phase droplets dispersed in air or an inert gaseous medium such as nitrogen. Under these conditions, the fog of water-immiscible fluid would act more like a gas, but would still be useful in practicing the invention.

Another type of water-immiscible medium which is suitably employed in certain embodiments of the invention is a supercritical fluid. A supercritical fluid is a dense gas that is maintained above its critical temperature (the temperature above which it cannot be liquified by any pressure). Such fluids are less viscous and diffuse more readily than liquids. Examples of supercritical fluids which are useful in practicing the present invention are carbon dioxide, and certain alkanes such as methane, ethane and propane. The conditions at which supercritical behavior is exhibited are known in the art. See, for instance, Smith U.S. Pat. No. 4,582,731 granted Apr. 15, 1986. Use of a supercritical fluid is advantageous in several ways. For example, supercritical fluids exhibit more gas properties than liquid properties and accordingly diffusion rates will be higher, and interaction rates correspondingly higher if they are diffusion-controlled. This results from the fact that liquids are by nature incompressible; there can be substantial resistance to diffusion across a boundary between a water-immiscible organic liquid and an aqueous phase. However, this is not the case with a supercritical fluid because it is compressible, thereby allowing for variation of the pressure exerted on the supercritical fluid and corresponding variation of the rate of diffusion, such that a pressure which maximizes the rate of diffusion can be applied. Additionally, solubility of certain species to be interacted is increased, and the controlling of the solubility of certain species to be interacted is facilitated, by use of supercritical fluids as compared to organic liquids. Also, the pressure-responsiveness of a supercritical fluid permits the convenient breaking of a microheterogeneous dispersion of aqueous phase in the fluid simply by manipulation of the pressure exerted on the fluid.

A key aspect of the invention is the surfactant-stabilization of a microheterogeneous dispersion of the aqueous phase containing an antibody or fragment thereof. The formation of a microheterogeneous dispersion of aqueous phase containing an antibody or antibody fragment in a functional state is directly dependent on the amount of surfactant used. Typically, the surfactant is present in at least the critical micelle concentration (which varies from surfactant to surfactant) and up to and including a concentration of 0.5 M. However, in successfully practicing the invention it is essential to consider not only the absolute amount of surfactant but also the ratio of the amount of water present to the amount of surfactant utilized. This ratio is referred to as $W_o$.

The selection of the ratio of water present to amount of surfactant is determined by a number of factors, the principal ones being protein (e.g. antibody or antibody fragment) size, the nature of the water-immiscible medium, the ionic strength of the aqueous phase, and the molecular radius of the protein. The desired effect of surfactant-stabilization is to maximize the amount of water-ensheathed antibody or antibody fragment in a functional state.

The closer the water to surfactant ratio ($W_o$) is to its optimal value, the greater the amount of aqueous phase particles containing antibody or antibody fragment in the functional state. A controlling factor is the amount of water in the aqueous phase particle as compared to the size of the protein (e.g. antibody or fragment) to be solubilized. The possible conditions in which the aqueous phase and antibody or antibody fragment can exist are principally as follows: the aqueous phase particles contain ample water for enveloping the antibody or fragment and preserving its functionality, and the ability of the antibody or fragment in each such particle to bind a species of interest is also optimal; the aqueous phase particles contain only a barely adequate amount of water in which to solubilize the antibody or fragment thereof, and thus the ability of the antibody or fragment to bind to one or more species of interest will be marginal; the aqueous phase particles will not contain enough water to envelope the antibody or fragment in the manner necessary to maintain it in a functional state. The closer the practitioner of the present invention comes to the optimal water/surfactant ratio, which varies from one system to another, the greater will be the number of aqueous phase particles containing optimally functional antibody or antibody fragment. On the other hand, the further away the practitioner moves from optimal values of the water/surfactant ratio, the fewer will be the number of aqueous phase particles which can accommodate an antibody or antibody fragment and preserve its functionality.

When one departs from the range of water/surfactant ratios which is suitable to get even a minimal number of aqueous phase particles containing ample water—or at least marginally adequate water—for antibody or fragment solubilization, the number of aqueous phase particles which can accommodate an antibody or fragment thereof and maintain its functionality in order for it to be useful in practicing the present invention will drop to an unacceptably low number and in some instances zero for practical purposes. Thus, the aqueous phase will not contain an effective amount of antibody or fragment in a functional state. This amount varies depending on the application to which the invention is put. One of ordinary skill in the art, having knowledge of the present invention, will be able to determine empirically what amount of functional antibody or antibody fragment is an effective amount for his purposes without undue experimentation.

The amount of surfactant utilized for stabilization in accordance with the present invention is typically in the water/surfactant molar ratio of 5:1–50:1. It can be appreciated by those of ordinary skill in the art that the optimal $W_o$ will vary from system to system, depending upon the size of the antibody or fragment employed (IgA, IgD, IgE and IgG antibodies all have molecular weights between 150K and 180K daltons, whereas IgM antibodies have a molecular weight of about 970K), the species of interest to be interacted with the antibody or fragment, temperature conditions, and the nature of the water-immiscible medium employed. Typically, the $W_o$ range is 7:1–45:1, more specifically 10:1–45:1, and even more specifically 15:1–40:1. For example, when employing sodium bi-(2-ethylhexyl)-sulfosuccinate in the hydrolysis of phenylacetate, the range of water/surfactant ratios which are useful is 21:1–31:1.

In practicing the invention, it is desirable to use a water/surfactant ratio which will result in a substantial number of the aqueous phase particles having an ample amount of water to envelope the antibody or antibody fragment and maintain it in a functional state. In certain embodiments of the invention, 80% of the aqueous phase particles maintain the antibody or fragment in at least a state of marginal functionality. However, in other embodiments of the invention it is sufficient if the water/surfactant ratio is sufficient to maintain at least about 50%, in some instances at least about 25%, and in yet other instances at least about 10%, of the aqueous phase particles in a condition which will preserve such functionality of the antibody or fragment. Looked at from another view, in certain embodiments the effective amount of antibody in a functional state (regardless of whether contained in a particle having ample water or only marginally adequate water) is at least 0.5%, preferably at least 1%, especially at least 10%, of the total antibody or antibody fragment present.

The surfactants employed are suitably anionic, such as sodium bi-(2-ethylhexyl)-sulfosuccinate ("AOT") and phospholipids, cationic, such as cetyltrimenthylammonium bromide ("cTAB") or chloride and methyltrioctylammonium chloride, or non-ionic, such as polyoxyethylene ethers. The choice is made based on which is the most beneficial to the achievement of the desired interaction and result. Theoretically, any molecule containing an aliphatic or aromatic moiety at one end of the molecule and a polar (either charged or neutral) moiety at the other can function as a surfactant. However, practically speaking the type of surfactant to be utilized is principally determined by the following factors: the antibody (or fragment)/antigen interaction desired, the pH of that interaction and the iso-electric point of the protein. The ordinarily skilled worker, equipped with the teachings herein, is capable of determining empirically which particular surfactant or surfactants (since the surfactants can be used in mixtures of two or more) is most suitable for his purposes without undue experimentation. Further examples of suitable anionic, cationic and non-ionic surfactants as well as of amphoteric surfactants which can also be used are set forth in the following table I:

TABLE I
CLASSIFICATION OF SURFACTANTS

| | ANIONIC | CATIONIC | NONIONIC | AMPHOTERIC |
|---|---|---|---|---|
| TYPE CHARGE IN SOLUTION | NEGATIVE | POSITIVE | NONE | POSITIVE OR NEGATIVE DEPENDING ON pH |
| TYPICAL STRUCTURES | $CH_3(CH_2)_nCOO^-Na^+$ n = 10 to 16 SOAPS<br><br>R—⟨benzene⟩—$SO_3^-Na^+$<br>LINEAR ALKYBENZENE SULFONATES<br><br>$[RO(CH_2CH_2O)_nSO_3^-X^+]$<br>n = 1-3<br>ALCOHOL ETHER SULFATES<br><br>$[ROSO_3^-X^+]$<br>ALKYL SULFATES<br><br>$[RSO_3^-X^+]$<br>PETROLEUM SULFONATES<br><br>$RCH(OH)(CH_2)_nSO_3^-X^+$<br>n = 2 OR 3<br>ALPHA OLEFIN SULFONATES<br><br>LIGNOSULFONATES<br><br>$[RO(CH_2CH_2O)_nPO_3H_2]$<br>PHOSPHATE ESTERS OF NONIONIC SURFACTANTS | $\left[\begin{array}{c}CH_3(CH_2)_{17}\\CH_3(CH_2)_{17}\end{array}\overset{CH_3}{\underset{CH_3}{N^+}}\right] Cl^-$<br>DISTEARYL DIMETHYL-AMMONIUM CHLORIDE<br><br>$\left[CH_3(CH_2)_{15}-\overset{CH_3}{\underset{CH_3}{N^+}}-CH_2-\text{⟨benzene⟩}\right] Cl^-$<br>CETYL DIMETHYL BENZYL-AMMONIUM CHLORIDE<br><br>$\left[\begin{array}{c}R-N\overset{+}{\underset{}{\phantom{x}}}\phantom{x}N-R\\\phantom{xxxx}R\end{array}\right] X^-$<br>IMIDAZOLINIUM DERIVATIVES | $CH_3(CH_2)_{10}CH_2O(C_2H_4O)_nH$<br>FATTY ALCOHOL ETHER<br><br>$RO(C_2H_4O)_nH$<br>ALKYLPHENOLIC ETHER<br><br>$CH_3(CH_2)_{11}N\begin{array}{c}(C_2H_4O)_nH\\(C_2H_4O)_nH\end{array}$<br>FATTY AMINE<br><br>$HO(C_2H_4O)_n(CHCH_2O)_n-$<br>$\phantom{xxxxxxxxxxx}(C_2H_4O)_nH$<br>$\phantom{xxxxxxxxxxx}CH_3$<br>POLYOXYPROPYLENE GLYCOL ETHER<br><br>$CH_3(CH_2)_{10}CONH(C_2H_4O)_nH$<br>FATTY AMIDE | $R-\overset{CH_3}{\underset{CH_3}{N^+}}-CH_2COO^-$<br>ALKYL BETAINE DERIVATIVES<br><br>$RN^+H_2CH_2CH_2SO_3^-$<br>AMINE SULFONATES<br><br>$RN^+H_2CH_2CH_2OSO_3^-$<br>FATTY AMINE SULFATES STRICTLY SPEAKING THE ALKYLBETAINES ARE ZWITTERIONIC, NOT AMPHOTERIC. IN THE BETAINES, THE CATION CANNOT BE NEUTRALIZED BY CHANGING THE pH. THESE MATERIALS ARE LISTED HERE BECAUSE OF THEIR STRUCTURAL SIMILARITY TO THE AMPHOTERICS |
| OTHER STRUCTURES | $RNHCH_2CH_2SO_3^-X^+$<br>TAURATES<br><br>$ROOCCH_2$<br>$\phantom{x}\vert$<br>$ROOCCHSO_3^-X^+$<br>SULFOSUCCINATES<br><br>$RCOOCH_2CH_2SO_3^-X^+$<br>ISETHIONATES | | $CH_3(CH_2)_{10}COO(C_2H_4O)_nH$<br>FATTY ESTER<br><br>$CH_3(CH_2)_{10}CON(C_2H_4OH)_2$<br>LAURIC DIETHANOLAMIDE<br><br>$CH_3(CH_2)_{11}-\overset{CH_3}{\underset{CH_3}{N}}\longrightarrow O$<br>LAURYL DIMETHYLAMINE OXIDE | |

The present invention can successfully be practiced with both polyclonal and monoclonal antibodies, as well as fragments of such antibodies (as previously described). Thus, antibodies such as IgM antibodies, which have a weight of approximately 970K daltons, can be solubilized if the water/surfactant ratio is sufficiently high. These high molecular weight IgM antibodies are often found in polyclonal antibody samples, and are in many instances a substantial component of the polyclonal antibody sample. However, it is more common and usually more desirable from the standpoint of ease of forming a suitable system, attainment of a high degree of specificity in the desired interaction, and reproducibility of the desired result, to utilize a monoclonal antibody. These samples contain only a single antibody which can be either an IgA, IgD, IgE or IgG (with molecular weights of 150K-180K daltons) or IgM. Of course, as understood by those of ordinary skill in the art, antibody fragments have molecular weights which are some fraction of the antibody from which they are derived.

As discussed in the preceding disclosure, the embodiments of the present invention have a wide-ranging utility in that the aforementioned system can be adapted to many different applications. The invention can be used in catalysis of interactions in which one or more reactants are converted to one or more desired products. In some embodiments one of the reactants can initially reside in a water-immiscible medium and/or at least one of the products can return to that medium after formation, but this is not a necessary condition to catalysis in accordance with the invention. A discussion of the subject of antibody catalysis and its uses is set forth in Massey et al. U.S. patent application Ser. No. 674,253, filed Nov. 27, 1984, the subject matter of which is incorporated by reference. Thus, the system of the present invention is useful in catalyzing reactions in which water is produced, such as the formation of peptide or phosphate linkages; reactions in which water is consumed, such as hydrolysis reactions; reactions in which a water-insoluble reactant is employed, such as steroid reductions; reactions in which one or more of the reactants are prostaglandins, alkanes, aromatics, and similar water-immiscible organic substances; and reactions in which substances reactive with water and thus unstable in it, such as chloroformate derivatives, are produced.

Additionally, the invention is suitable for carrying out operations in which the antibody or antibody fragment in the aqueous phase binds with one or more species in the water-immiscible medium. Such operations are of importance, for example, in carrying out assays. The binding affinity of the antibody or fragment for these species of interest is preserved in connection with practicing the present invention, and thus provides a highly sensitive technique for use in performing assays, such as by an ELISA analysis. In yet another embodiment of the invention, a catalytic antibody or antibody fragment temporarily binds with a species of interest, and that binding event causes the occurrence of some signal indicating the presence of the species, such as formation of a telltale reaction product. The antibody or fragment, now once again free to bind, repeats the cycle with yet unreacted species. An integration over time of the signal given off as a result of binding is a measure of the amount of species present.

Yet another manner in which the present invention can be effectively employed is to isolate a protein or non-protein species of interest from a mixture of substances containing it, with optional concentration of the isolate(s). These embodiments take advantage of the fact that a system in accordance with the present invention can be designed so that protein or non-protien species of particular interest can be selectively sequestered in aqueous phase particles while other protein and/or non-protein substances, as the case may be, are excluded. There are several factors which control the selectivity and efficiency of such embodiments. Principally, they are the binding affinity of the antibody or antibody fragment for the protein or non-protein of interest, the iso-electric point of the protein, the size of the protein or non-protein, the hydrophobic or hydrophilic nature of the protein or non-protein of interest, the respective ionic strength and pH value of the aqueous phase particles, the size of the aqueous phase particles, the charge of the aqueous phase particles and temperature. After binding, the complex or conjugate formed with the protein or non-protein is recovered from the system, for instance, by precipitating it out with the addition of a sufficiently large amount of aqueous salt solution, such as a solution of potassium chloride. The complex or conjugate can then be disassociated by conventional means. During or after recovery of the isolate(s), concentration can be effected if desired. In light of the teachings herein, one of ordinary skill in the art will be able to adapt the embodiments described above without undue experimentation.

Accordingly, the invention also encompasses a method in which an antibody or fragment thereof which is surfactant-stabilized in a microheterogeneously disperse aqueous phase interacts with one or more species having access to the antibody, for example because they are in a water-immiscible medium in which such dispersion is formed. As is clear, the amount of antibody or antibody fragment in a functional state is sufficient to effect the desired interaction. The method is conducted at conditions (for instance, temperature, pH, ionic strength of the aqueous phase, etc.) which are effective to bring about such interaction for a time sufficient for the interaction to occur (including without limitation, and depending on the particular interaction, times ranging from fractions of a second (e.g. 1 msec) to several hours (e.g. 10 hours)).

Certain particularly advantageous methods are those in which a catalytic antibody is used to effect the conversion of one or more reactants into one or more desired products; in which the antibody in the aqueous phase is utilized to bind with a species of interest for purposes of assaying that species; and in which the antibody in the aqueous phase is used to bind to a protein substance—or non-protein substance for example, one contaminating a protein-containing medium. The resulting complex or conjugate is the recovered, the antibody component removed, and the protein or non-protein species isolated, optionally as a concentrate.

As previously noted, the invention is also in a method for producing the interaction system comprising an antibody or antibody fragment in a functional state contained in a microheterogeneously dispersed aqueous phase. Any method by which an effective amount (as previously discussed) of antibody or antibody fragment is retained in an aqueous solution is suitable for practicing the present invention. The essential step in the method of producing the system in accordance with the present invention is surfactant-stabilizing the microheterogeneous dispersion of the aqueous phase containing an amount of antibody or antibody-fragment in a functional state sufficient to effect the desired interaction. Conditions governing these embodiments are temperature, pressure, buffer strength, and the composition of the atmosphere (especially if a gaseous component thereof is a co-reactant). Three advantageous methods which can be utilized to achieve this are described below.

In one, an interaction system including an antibody, or antibody fragment as discussed in preceding paragraphs, is formed by injecting an aqueous solution of the antibody or antibody fragment into a solution of a surfactant in a water-immiscible fluid or a water-immiscible supercritical fluid. The surfactant is present in an amount sufficient to effect the formation of a surfactant-stabilized microheterogeneous dispersion of aqueous phase in the fluid employed, and is also present in an amount sufficient to cause the aqueous phase to contain an amount of antibody or antibody fragment in a functional state sufficient for effecting the desired interaction.

In another embodiment of the method for forming an interaction system in accordance with the invention, a freeze-dried antibody or antibody fragment in powder form is added to a surfactant-stabilized microheterogeneous dispersion of an aqueous phase in a water-immiscible medium. Then, the protein powder is mixed with the microheterogeneous dispersion of the aqueous phase in the medium to form a microheterogeneous surfactant-stabilized dispersion of aqueous phase, with the surfactant being present in an amount sufficient to stabilize the dispersion and cause it to contain an amount of antibody or antibody fragment in a functional state sufficient to effect the interaction.

Yet another embodiment of the method of forming an interaction system in accordance with the present invention is one in which an aqueous solution of an antibody or antibody fragment and a solution of a surfactant in a water-immiscible medium are combined, and then the combination is agitated to form in the medium a surfactant-stabilized microheterogeneous dispersion of aqueous phase, with the antibody or antibody fragment contained in such phase. The water in the aqueous phase and the surfactant are provided in relative amounts sufficient to stabilize the microheterogeneous dispersion and cause it to be capable of containing an amount of antibody or antibody fragment in a functional state sufficient to effect the desired interaction.

Additional objects, advantages and details relating to the practice of the present invention will be evident from the following examples.

EXAMPLE 1

Demonstration of Antibody Catalytic Activity in Iso-octane

A solution of the 48-G7 antibody was purified from ascites fluid by Protein A chromatography. Following dialysis of the IgG fractions which were obtained into 10 mM tris buffer, 4.0 ml of a 3.0 mg/ml solution of this protein was lypholyzed to dryness. The protein powder was then resuspended in 1.5 ml of 10 mM tris buffer (pH 8.5). When 10 $\mu$l of this antibody solution was added to one milliliter of buffer, a protein concentration of 0.090 mg/ml resulted (as determined from 280 nm and 260 nm absorbances). Thus, the stock antibody solution was 9.0 mg/ml.

The rate of antibody catalyzed hydrolysis of p-nitrophenylcarbonate was determined by adding 15 $\mu$l of a 50 mM p-nitrophenylcarbonate (p-NPC) solution dissolved in tetrahydrofuran to 3.0 ml of 10 mM tris buffer (pH 8.5). After this solution was mixed to homogeneity, 1.0 ml was transferred into a reference cuvette and 1.0 ml was transferred into a sample cuvette. An assay was initiated by addition of 10 $\mu$l of the 48-G7 antibody solution (0.090 mg). The progress of the reaction was monitored with a Hitachi Model 3200 double beam spectrophotometer (to screen out the rate of solvent-induced background hydrolysis) at 400 nm. The extinction coefficient for the product, p-nitrophenol, was 18,300 $M^{-1} cm^{-1}$ at pH 8.5.

Figure 2:
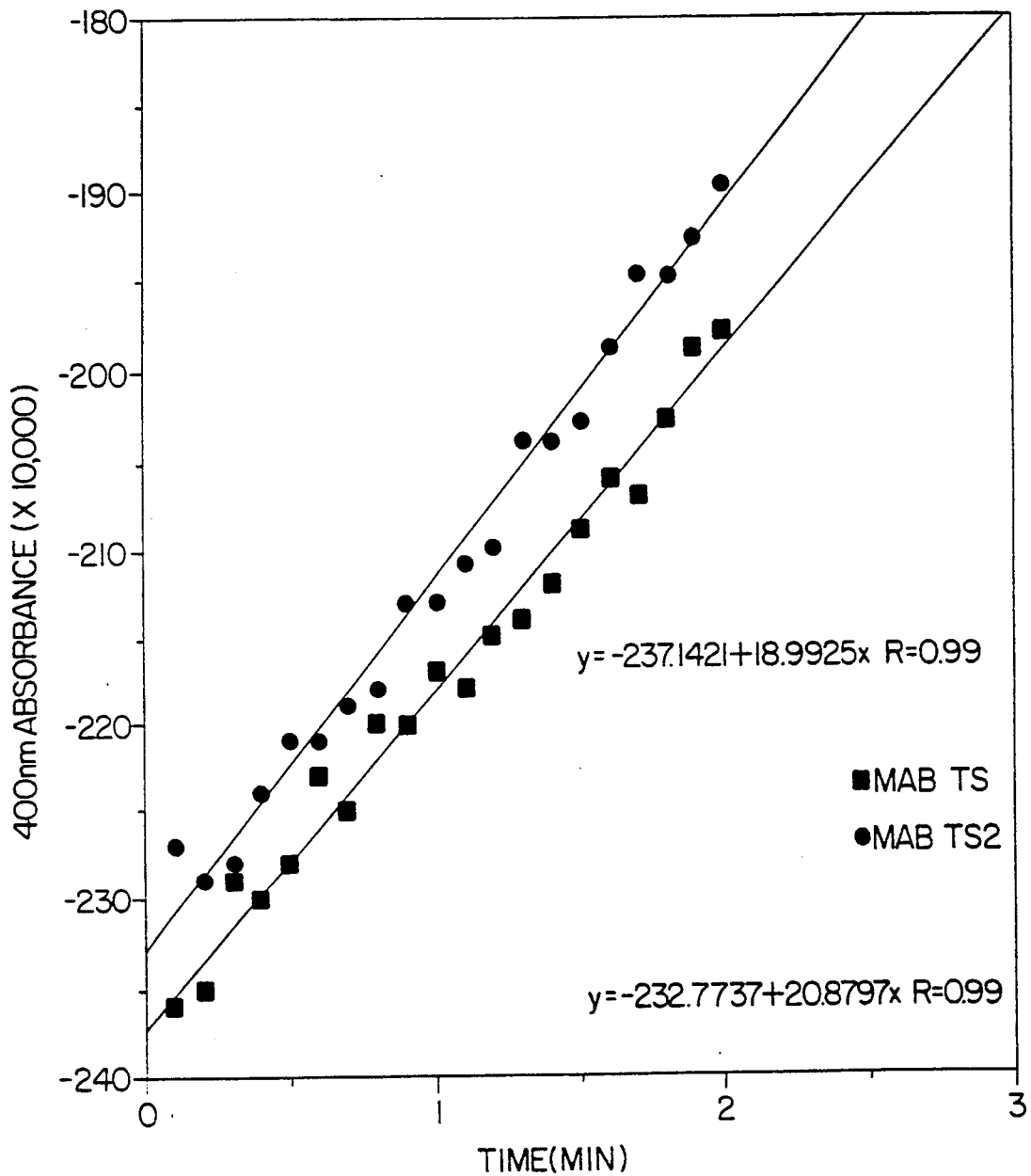
FIG. 2 is a set of curves showing the results of the hydrolysis reaction with the same concentration of reactant and antibody catalyst in aqueous solution also containing 24 $\mu$M transition state analog inhibitor.

As shown in FIG. 1, under these conditions 90 $\mu$g/ml of 48-G7 antibody hydrolyzes 0.49 $\mu$molar p-NPC (0.0089 Abs/min) per minute. However, when the reaction was repeated under the same conditions, except for the addition in the second instance of 24 $\mu$M p-nitrophenylphosphonate (the eliciting hapten or transition state analog which competitively bound with the antibody, delivered from a 2.4 mM stock solution dissolved in 10 mM tris buffer (pH 8.5)), the rate of hydrolysis was significantly reduced to 0.002 Abs units/minute or 0.109,$\mu$molar/minute. This is shown in FIG. 2. The hapten-induced inhibition of the hydrolysis demonstrates that catalysis was occurring at the antigen binding site of the 48-G7 antibody.

The rate of 48-G7 antibody-catalyzed hydrolysis of p-NPC was determined in a 50 mM solution of sodium bi-(2-ethylhexyl) sulfosuccinate ("AOT") in iso-octane containing 888 $\mu$M of p-NPC. First 20 ml of the iso-octane solution containing 0.445 g of AOT (M.W.=445g) and 3.5 mg of p-NPC (M.W.-197g) were prepared. To this solution 10 $\mu$l mM of 10 mM 10 tris buffer (pH 8.5) and 10 $\mu$l of the 48-G7 antibody solution were added. A microemulsion of disperse aqueous phase in the iso-octane was obtained by mixing. The hydrolysis of p-NPC and the production of p-nitrophenol was monitored at 400 nm, although an accurate conversion between 400 nm absorbance and moles of p-nitrophenol formed was not possible because the pH inside the microemulsified aqueous phase particles could not be accurately determined.

Figure 3:
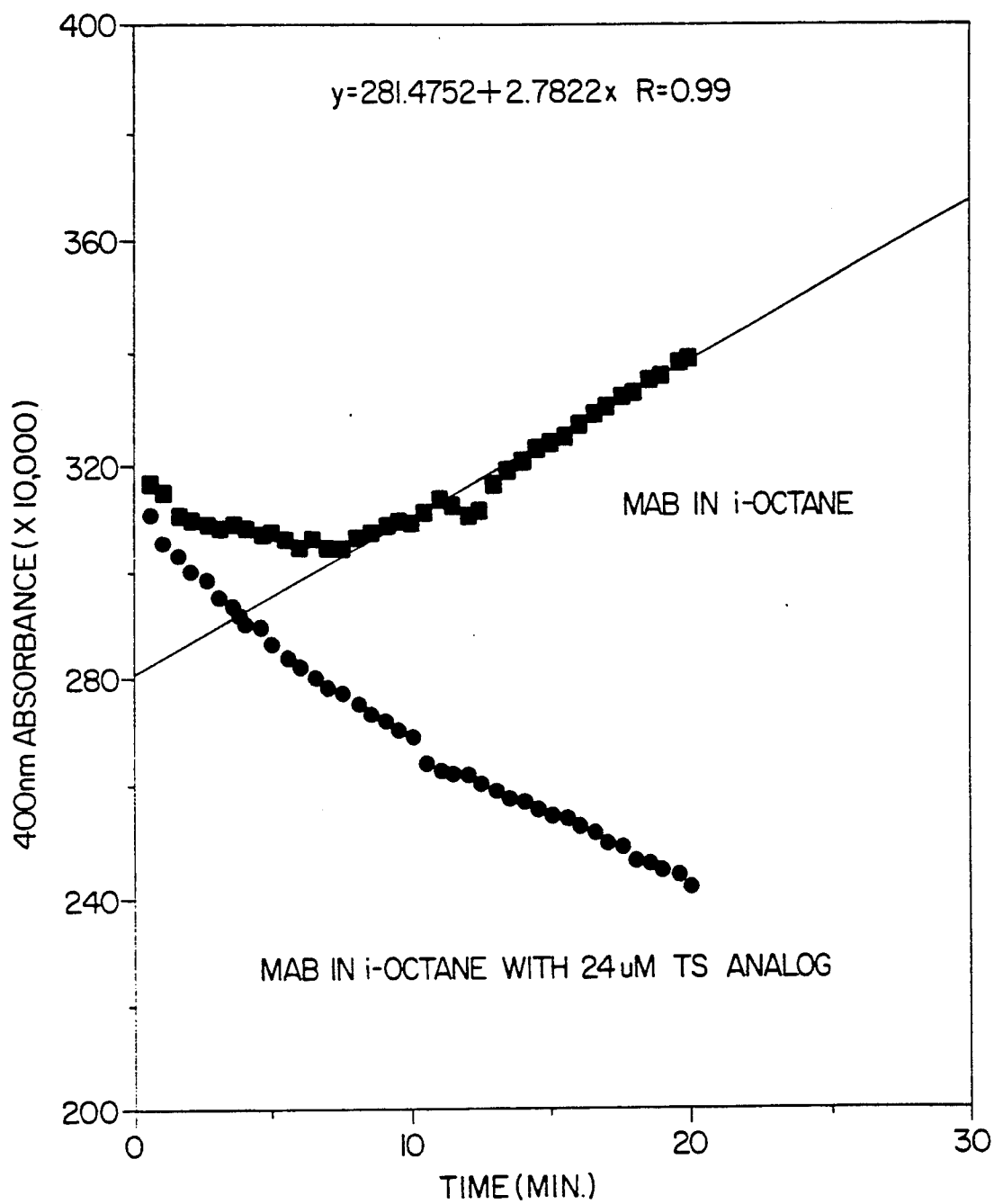
FIG. 3 is a set of curves comparing the progression of an antibody-catalyzed hydrolysis reaction in the microemulsion in accordance with the invention and a similar antibody solution inhibited by 24 $\mu$M transition state analog.

Upon addition of the 48-G7 antibody solution, the biphasic system became turbid as the antibody-containing, microemulsified aqueous phase particles formed. This was reflected in a decrease in 400 nm absorbance during the first seven minutes of the experiment, as shown in FIG. 3. Subsequently, absorbance at 400 nm began to increase as p-nitrophenol was formed. The rate of 400 nm absorbance increase was 0.00028 Abs/minute.

When this experiment was repeated with the 10,$\mu$l of tris buffer containing 2.4 mM p-nitrophosphonate hapten (24 $\mu$M final concentration), the initial 400 nm absorbance was similar to the non-inhibited antibody solution. However, unlike the non-inhibited antibody solution, the 400 nm absorbance did not rise after seven or even twenty minutes. Instead, the 400 nm absorbance continued to decrease. This was indicative of continued microemulsion formation without p-nitrophenylcarbonate hydrolysis. The experiment also demonstrated that p-nitrophenylcarbonate hydrolysis did not occur in the iso-octane microemulsion when the 48-G7 antibody did not retain its catalytic activity. It further demonstrated that solvent-induced background hydrolysis of p-nitrophenylcarbonate was eliminated, since even when the antibody was inhibited there was no appreciable hydrolysis. Thus, the rate of antibody catalyzed hydrolysis of p-nitrophenylcarbonate could be determined in a single beam spectrophotometric mode when the reaction was performed in a water/iso-octane microemulsion.

EXAMPLE 2

Recovery of Active Antibodies From A Non-Polar Solvent

Summarizing for context, we note that in this example unmodified monoclonal IgG antibodies 48-G7, made against a p-nitrophenylphosphonate hapten, and 20-G9, made against a phenylphosphonate hapten (and therefore a non-p-nitrophenylcarbonate control), were each dissolved in a 50 mM solution of sodium bi-2-(ethylhexyl)-sulfosuccinate ("AOT") in iso-octane. The 48-G7 and 20-G9 antibodies were each subsequently recovered from their respective microemulsion solutions by adding a buffered aqueous salt solution into which they partitioned. These recovered antibodies maintained their reactivity as shown in an enzyme linked immunosorbant assay (ELISA).

More specifically, the 48-G7 and 20-G9 antibodies were purified by Protein A affinity chromatography and then separately sealed within dialysis membranes (Spectra Por 23 mm, 6-8K dalton cutoff) and dialyzed with constant stirring for 7 hours at 4° C. against 1.5 L of 10 mM tris-HCl (pH 8.4). Protein concentrations of 3.8 and 3.4 mg/ml were determined for the 48-G7 and 20-G9 antibodies, respectively, by ultraviolet light absorption at 260 nm and 280 nm.

Before the antibodies were added into iso-octane, 15 µl of water were added to 1.0 ml of an iso-octane solution containing 50 mM AOT (0.445 g/; 20 ml of iso-octane). Five µl samples each of the 48-G7 and 20-G9 antibodies (7.6 nmoles of binding sites per 5 µl of 48-G7 antibody) were added to 1.0 ml samples of this 50.0 mM AOT solution in iso-octane and mixing was achieved by pipetting several times with Pastuer pipets. These solutions were sealed in 1.0 ml spectrophotometric cuvettes and then stored in the dark at room temperature. After 30 minutes the iso-octane solutions were entirely clear. This was indicative of the fact that an antibody-containing microemulsion had formed.

100 µl of a 10 mM tris-HCL, 150 mM KCl (pH 7.4) buffer was then introduced in each cuvette. The aqueous (bottom) phase was recovered from each cuvette by microliter syringe. As a control, 5 µl of the 48-G7 and 20-G9 antibodies were added to respective 100 µl portions of the 10 mM Tris-HCl, 150 mM KCL (pH 7.4) buffer for subsequent comparison of antibody binding activity (with and without incubation in a water/iso-octane microemulsion). The concentration of recovered protein was then determined by a BioRad coomassie blue protein assay with varying aliquots (0–30 µg) of bovine IgG (BioRad Standard I) as the protein standard. Antibody samples in 10 mM tris-HCl, 150 mM KCl (pH 7.4) buffer and antibody samples recovered from the AOT/iso-octane microemulsion into 10 mM tris-HCl, 150 mM KCl (pH 7.4) buffer were diluted ten-fold with phosphate buffered saline solution (2.7 mM KCl, 1.8 mM $KH_2PO_4$, 138 mM NaCl, 8 mM $Na_2HPO_4$). Antibody samples and standards (0.8 ml) and coomassie blue dye (0.2 ml) were mixed and incubated for 30 minutes at room temperature. Subsequently their 595 nm absorbance was determined on a Beckman DU-50 spectrophotometer. Protein recovery from AOT/iso-octane was determined by comparison with the protein standards as shown in Table II.

TABLE II

PROTEIN RECOVERY

| Antibody Sample | Protein Recovered (g/ml) | % Recovery |
|---|---|---|
| 48-G7 Control (not added to iso-octane) | 311 | — |
| 48-G7 (After iso-octane) | 22 | 7.1 |
| 20-G9 Control (not added to iso-octane) | 144 | — |
| 20-G9 (After iso-octane) | 23 | 16.0 |

The binding ability of the recovered antibodies was measured in an ELISA analysis. Microtiter 96 well ELISA plates (Corning) were treated for 24 hours at 4° C. with either 0.20 µg bovine serum albumin or 0.20 µg of hapten covalently linked to keyhole limpet hemocyanin per well in carbonate buffer (35 mM $NaHCO_3$, 15 mM $Na_2CO_3$, pH 9.6). Plates were washed 3 times with 350 µl of PBS+0.05% Tween 20 buffer per well. Any remaining binding sites on the ELISA plates were blocked by adding 100 µl of PBS+2% bovine serum albumin+0.05% Tween 20 buffer per well and incubating for 2 hours at 36° C. The wells were then emptied and blotted dry. Control proteins (both the 48-G7 and 20-G9 monoclonal antibodies not added to the AOT-/iso-octane solution), and the antibody samples recovered from the iso-octane microemulsion, were serially diluted by tenfold in PBS+0.05% Tween 20 buffer. Antibody samples were then added to ELISA plates at 50 µl per well and incubated for 1 hour at 36° C. Plates were washed 3 times (as above). A goat anti-mouse IgG peroxidase conjugate (Kirkegaard and Perry Laboratories) was added to each well and incubated for 1 hour at 36° C. Plates were washed 3 times (as above). To each ELISA well 50 µl of substrate (hydrogen peroxide, 2,2'-azino-di-(3-ethyl-benzthiazoline sulfonate, Kirkegaard and Perry Laboratories) was added and incubated for an additional 30 minutes at room temperature. Absorbance of light at 414 nm was used as a quantitative measure of active antigen binding ability. As shown below in Table III, the 48-G7 antibody retained its antigen-binding capability after recovery from iso-octane.

TABLE III

ANTIBODY BINDING TO p-NITROPHENYLPHOSPHONATE-KLH

| Antibody Sample | Mean (n = 2) 414 nm Absorbance at 1/10,000 Antibody Dilution | % Binding Efficiency |
|---|---|---|
| 48-G7 (not added to iso-octane) | 0.954 | 100% |
| 48-G7 (after iso-octane) | 0.766 | 80% |
| 20-G9 (not added to iso-octane) | 0.332 | 35% |
| 20-G9 (after iso-octane) | 0.276 | 29% |

EXAMPLE 3

Determining the Optimum Water to Detergent Ratio ($W_o$) for a Phenylacetate Hydrolyzing Antibody in Iso-Octane Preparation of AOT Surfactant The AOT surfactant was obtained from Pfaltz and Bauer, Inc. (Cat. #D48645) and purified via the method of Kotlarchyk et al. (Physical Review A. 1984, 29, 2054-2069) as follows.

Fifty grams of the surfactant was dissolved in approximately 200 grams of absolute methanol by stirring at room temperature for 10 minutes. The resulting solution was then filtered by gravity through a medium-fine grade filterpaper. The resulting solid was resuspended in another 200 ml of absolute methanol and gravity filtered through a medium-fine paper filter again. The resulting solution was then rotor evaporated to dryness and the resulting solid was resuspended in 50 ml of hexane. To the resulting solution 10 grams of activated charcoal was added and after stirring at room temperature for 2 minutes, the charcoal was removed by gravity filtration through a medium-fine filterpaper. The solid AOT was then recovered from the hexane solution by rotor evaporation. The resulting solid was then vacuum dried at about 50 mTorr and room temperature for 24 hours. The resulting AOT powder which contains a 1:1 mole amount of water (Kotlarchyk et al.), was rapidly placed in an air-tight bottle within a dessicator.

Monoclonal Antibody Preparation

The 20-G9 antibody was isolated from ascites fluid by Protein A chromatography (Bio-Rad; #153-6153). This involved pre-equilibration of the 5.0 ml column with 100 ml of pH 9.0 binding buffer (Bio-Rad; #153-6161) followed by 15 ml of ascites fluid mixed with 15 ml of binding buffer. After the column was washed with another 100 ml of binding buffer the monoclonal antibody was eluted with Bio-Rad elution buffer (Cat #153-6162) and recovered in 2.1 ml aliquots collected into 1.6 ml volumes of 1.0M tris buffer (pH 9.0). Fractions with protein concentrations over 2.0 mg/ml (as determined by the ratio of the absorbances at 280 nm and 260 nm) were combined and dialyzed into 20 mM tris buffer pH 8.5. The resulting protein solution was then lypholyzed to dryness in a FTS System, Inc. Flexi-Dry apparatus. The resulting protein powder was resuspended in sufficient 20 mM tris buffer, pH 8.5, to yield a protein concentration of 27.4 mg/ml.

Hydrolysis of Phenylacetate by the 20-G9 Antibody Dissolved in a 50 mM AOT Iso-octane Solution A solution of 50 mM AOT in iso-octane was prepared by mixing 0.445 g of AOT into 20 ml of iso-octane (Cat. #15,501-2; 2,2,3-trimethylpentane, Aldrich Chemical Co.). To this solution sufficient phenylacetate (Sigma Chem. Co., Cat. No. P 2396) was added to yield a solution of 280 µM (as judged by the absorbance at 264 nm). Solutions containing different water to surfactant ratios ($W_o$) were prepared by the following recipes:

TABLE IV

| (Iso-Octane) | Monoclonal Antibody 20-G9 | Buffer 20 mM Tris | Total Added | $W_o$* |
|---|---|---|---|---|
| 991 µl | 3.5 µl | 5.5 µl | 9.0 µl | 11 |
| 986.5 µl | 3.5 µl | 10 µl | 13.5 µl | 16 |
| 982 µl | 3.5 µl | 14.5 µl | 18.0 µl | 21 |
| 980 µl | 3.5 µl | 17 µl | 20.5 µl | 23.5 |
| 977.5 µl | 3.5 µl | 18.0 µl | 22.5 µl | 26 |
| 975 µl | 3.5 µl | 21.5 µl | 24.8 µl | 28.5 |
| 973 µl | 3.5 µl | 23.5 µl | 27 µl | 31 |
| 968.5 µl | 3.5 µl | 28.0 µl | 31.5 µl | 36 |

*Note the calculated water:surfactant ratios include the contribution of 1 mole of water added per mole of surfactant, which is present in the vacuum-dried AOT solid.

The order of addition was, first, preparation of the 50 mM AOT/iso-octane solution (40 ml), and then addition of phenylacetate. One ml aliquots were distributed into 1.0 ml cuvettes and the appropriate amount of buffer was added to the iso-octane solution, without stirring. Finally, the reaction was initiated by addition of 3.5 µl of monoclonal antibody (96 µg). After shaking for 10 seconds the reaction vessel was placed in a single beam spectrophotometer (Hitachi Model #3200) and the increase in absorbance was monitored at 270 nm. (Subtraction of the background rate of phenylacetate hydrolysis (uncatalyzed) was not necessary because under these conditions no phenylacetate hydrolysis was observed over a period of 12 hours (data not displayed).)

The catalyzed reaction is:

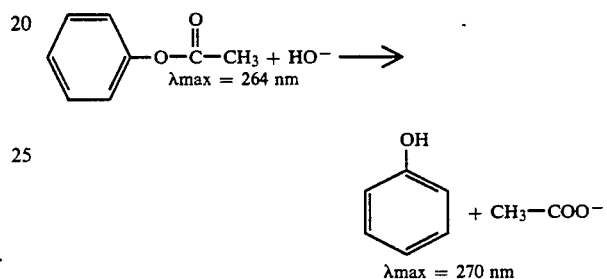

Figure 4:
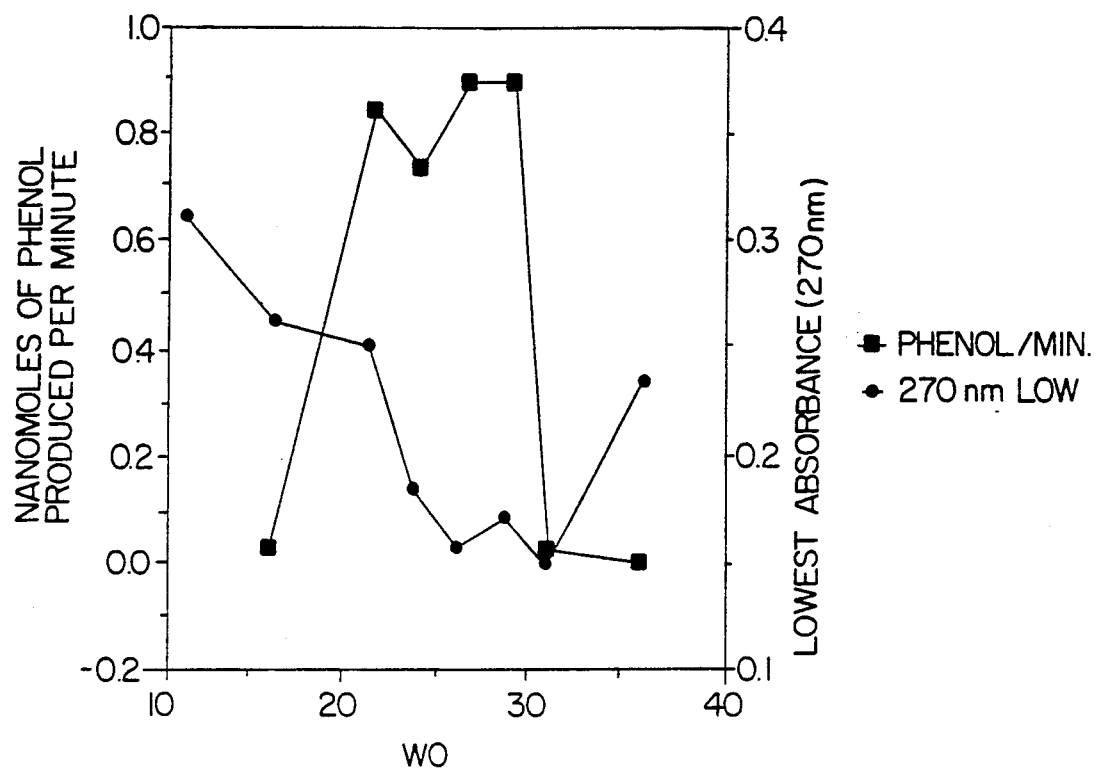
FIG. 4 is a set of curves showing the effect of varying the water to surfactant ratio on antibody activity and reverse micelle formation (by absolute 270 nm absorbance).

The data in Table IV and FIG. 4 were determined by monitoring the increase in 270 nm absorbance every two minutes for at least 30 minutes.

TABLE V

| Antibody Catalyzed Hydrolysis of Phenylacetate as a Function of $W_o$ | | |
|---|---|---|
| $W_o$ (Lowest 270 nm Abs.) | Change in 270 nm Absorbance/Min | Nanomoles of Phenol Produced per Minute |
| 11 (0.3099 Abs) | −0.0002 | None |
| 16 (0.2624 Abs) | +0.00006 | 0.03 |
| 21 (0.2502 Abs) | 0.0016 | 0.84 |
| 23.5 (0.184 Abs) | 0.0014 | 0.73 |
| 26 (0.1583 Abs) | 0.0017 | 0.89 |
| 28.5 (0.1722 Abs) | 0.0017 | 0.89 |
| 31 (0.1492 Abs) | +0.0005 | 0.026 |
| 36 (0.2351 Abs) | −0.0026 | None |

The ratio of water to detergent ($W_o$) was critical to determining the extend of both antibody activity and microemulsion formation. While the monoclonal antibody at a $W_o$ of 16 was not catalytic, at a $W_o$ of approximately 21 the antibody was catalytic. Consistent with these findings is the lowest 270 nm absorbance observed during each kinetic run, which reflects both the concentration of phenylacetate and phenol in the cuvette (which is effectively consistent for each cuvette) as well as the turbidity of the solution. Turbidity is indicative of the effectiveness of forming antibody microemulsion; the highest activity antibody solutions have the lowest absolute absorbance at 270 nm. Thus, below a $W_o$ of 21 and above a $W_o$ of 31 functionality of the antibody is not favored. Instead, denatured protein solutions result. This effect is most likely related to the large molecular weight of the antibodies and would cause other protein solutions containing antibodies as a major component to exhibit corresponding behavior as a function of $W_o$.

EXAMPLE 4

Transition State Analog Inhibition of Phenylacetate Hydrolyses by Monoclonal Antibody 20-G9 Within a Microemulsion The antibody 20-G9 was obtained by immunization of mice to a phenylphosphonate hapten followed by the normal procedures of hybridoma fusion and monoclonal antibody screening by ELISA analysis for antigen and hapten binding. The final preparation of this antibody involved Protein A column chromatography, combination of fractions with protein concentrations greater than 2.0 mg/ml, dialysis into 20 mM tris buffer pH 8.5, and finally lyophilization in a FTS TM Systems, Inc. Flexi-Dry apparatus. The resulting protein powder was resuspended in 78 μl of 20 mM tris buffer pH 8.5. This solution was divided into two equal parts and to each fraction 30 μl 20 mM tris buffer containing 1.22 mM transition state analog (i.e., the eliciting hapten) were added. The protein concentration of these solutions was determined to be 60 mg/ml by differential absorbance at 280 nm and 260 nm.

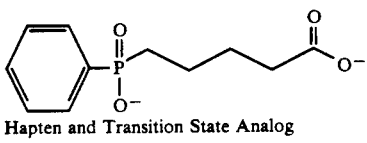

Hapten and Transition State Analog

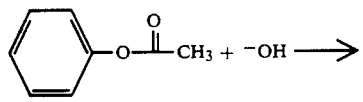

$\lambda = 264$ nm ($\epsilon = 501$ M$^{-1}$ cm$^{-1}$)
Antibody Catalyzed Reaction

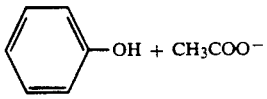

$\lambda = 270$ nm ($\epsilon = 1905$ M$^{-1}$ cm$^{-1}$)

A solution of 50 mM AOT in iso-octane was prepared by dissolving 0.89 g of AOT in 40 ml of iso-octane. To this solution sufficient phenylacetate was added to yield a final substrate concentration of 155 μM (0.0775 Abs. units at 264 nm).

Figure 5:
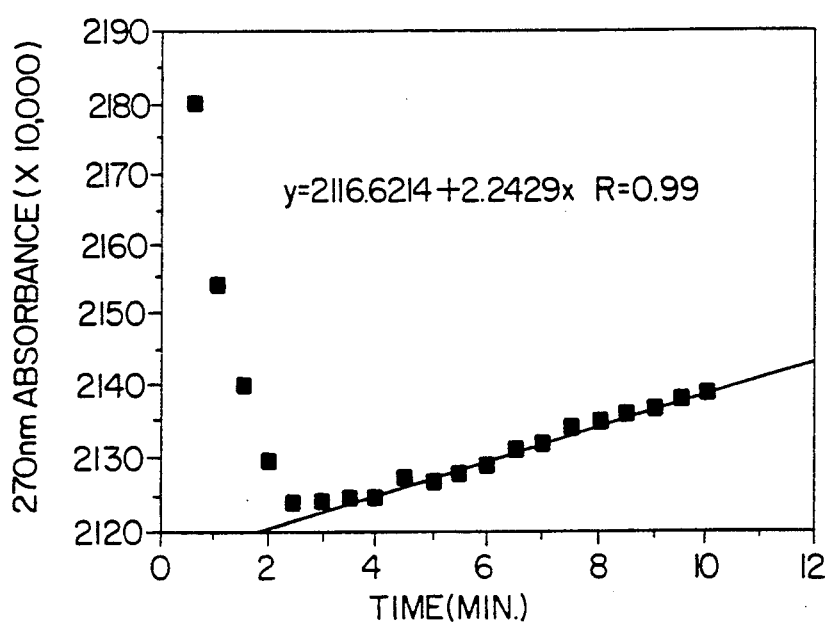
FIG. 5 is a curve showing progression of a hydrolysis reaction catalyzed with 20-G9 antibody in the microemulsion phase in accordance with the invention.

The antibody catalyzed hydrolysis of phenylacetate was initiated by adding 1 μl of monoclonal antibody (about 60 μg) to a solution containing 24 μl of tris buffer, 155 μM phenylacetate and 50 mM AOT ($W_o = 27.8$) dissolved in 1.0 ml of iso-octane. The change in 270 nm absorbance was monitored at 30 second intervals for 10 minutes. These measurements were performed in a Hitachi 3200 spectrophotometer in the single beam mode, because prior experiments demonstrated that spontaneous decomposition of phenylacetate (i.e., background hydrolysis) did not occur in the microemulsion during the time period of our rate measurements. Thus, a blank or reference solution was not required. Changes observed in the 270 nm absorbance during each kinetic run, as shown in FIG. 5, reflected both the formation of a microemulsion (resulting in an absorbance decrease) and phenol production (resulting in an absorbance increase).

Again referring to FIG. 5, 155 M phenylacetate (PA) was hydrolyzed by 60 μg of 20-G9 antibody at a rate of about 0.00022 Abs. units/minute (or 0.12 nanomoles/minute). Any "burst reaction" caused by the antibody hydrolysis of substrate was hidden by the decreased 270 nm absorbance which occurred during the first two minutes of the rate assay.

In contrast, the presence of 29 μmolar hapten totally inhibited the 20-G9 catalyzed hydrolysis of phenylacetate. See the results depicted in FIG. 6. The observed change in 270 nm absorbance ( 0.0001 Abs. units per minute) was caused by continued decrease in solution turbidity as the antibody microemulsion formed. No background hydrolysis of phenylacetate was observed during this experiment, which is consistent with previous experiments on the spontaneous rate of phenylacetate hydrolysis in a microemulsion.

The results presented above demonstrate that antigen-antibody complexes were formed in solutions of AOT in iso-octane. Thus, both the immunological and catalytic functions of antibodies can be maintained in a microemulsion environment. The precise conditions used in this study were: 60 μg of antibody, 25 μl of water ($W_o = 27.8$) dissolved in 50 mM AOT, 155 μM phenylacetate and an iso-octane solvent.

An additional point of interest was the lack of background or spontaneous phenylacetate hydrolysis observed when the substrate was dissolved in a microemulsion system. This result would appear to require a re-ordering of the way in which antibody catalyzed reactions are described. Conventionally, the efficiency of an antibody-catalyzed reaction is reported in the literature as an acceleration factor which is defined by the ratio of the rate constant for the antibody catalyzed reaction ($k_{cat}$) divided by the rate constant for the background hydrolysis reaction ($k_{uncat}$). In the scientific literature the value of this constant acceleration factor is said to be between a few hundred and several million for different antibody catalyzed reactions. Clearly, in a microemulsion in accordance with the invention the value of $k_{uncat}$ goes to zero, and therefore the rate constant acceleration factor becomes so large that it is undefined.

The industrial significance of this observation is that reactions which might occur in solution in a non-stereospecific manner, and formerly would have competed with a stereospecific antibody-catalyzed (or antibody-fragment-catalyzed) reaction, can now be avoided. This would permit the synthesis of a single steroisomer, instead of a racemic mixture, by the catalytic antibody or antibody fragment techniques of the present invention.

We claim:

1. An interaction system, including an antibody or antibody fragment having functional capability, which comprises a surfactant-stabilized microheterogeneous dispersion of aqueous phase in a water-immiscible medium, said aqueous phase containing an amount of said antibody or said fragment in a functional state sufficient to effect the interaction; wherein said antibody or antibody fragment is adapted to effect a catalytic conversion of one or more reactants into one or more products.

2. A system as defined in claim 1, wherein said aqueous phase particles contain a monoclonal antibody, a polyclonal antibody, monoclonal antibody fragment or polyclonal antibody fragment.

3. A system as defined in claim 2, wherein said antibody is a monoclonal antibody.

4. A system as defined in claim 1, wherein said surfactant is anionic.

5. A system as defined in claim 1, wherein said surfactant is cationic.

6. A system as defined in claim 1, wherein said surfactant is neutral or amphoteric.

7. A system as defined in claim 1, wherein the water-immiscible medium is a water-immiscible fluid or a water-immiscible supercritical fluid.

8. A system as defined in claim 1, wherein the molar ratio of water to surfactant is in the range from 5:1 to 50:1 inclusive.

9. A system as defined in claim 1, which comprises a surfactant-stabilized microheterogeneous dispersion of aqueous phase particles in an organic liquid selected from the group consisting of aromatics, substituted aromatics, alkanes, substituted alkanes, ethers, and acetone.

10. In a water-immiscible medium, an interaction system including an antibody or antibody fragment having functional capability, which comprises a plurality of surfactant-stabilized microheterogeneously disperse aqueous phase particles, said particles containing an amount of said antibody or said fragment in a functional state sufficient to effect said interaction; wherein said antibody or antibody fragment is adapted to effect a catalytic conversion of one or more reactants into one or more products.

11. A system as defined in claim 10, wherein said aqueous phase particles contain a monoclonal antibody, a polyclonal antibody, monoclonal antibody fragment or polyclonal antibody fragment.

12. A system as defined in claim 11, wherein said antibody is a monoclonal antibody.

13. A system as defined in claim 10, wherein said surfactant is anionic.

14. A system as defined in claim 10, wherein said surfactant is cationic.

15. A system as defined in claim 10, wherein said surfactant is neutral or amphoteric.

16. A system as defined in claim 10, wherein the water-immiscible medium is a water-immiscible fluid or a water-immiscible supercritical fluid.

17. A system as defined in claim 10, wherein the molar ratio of water to surfactant is in the range from 5:1 to 50:1 inclusive.

18. A system as defined in claim 10, in an organic liquid selected from the group consisting of aromatics, substituted aromatics, alkanes, substituted alkanes, ethers, acetone, and dioxane.

19. A system for interacting a catalytic antibody, or catalytic antibody fragment with a reactant, which comprises a surfactant-stabilized microheterogeneous dispersion of aqueous phase in a water-immiscible medium, said aqueous phase containing an amount of said catalytic antibody or catalytic antibody fragment sufficient to effect said catalysis.

20. A system as defined in claim 19, wherein said microheterogeneous dispersion of aqueous phase is a microemulsion or a dispersion of aqueous reverse micelles, said aqueous phase contains a catalytic monoclonal antibody, and is adapted for the conversion of one or more reactants to one or more products.

21. A system as defined in claim 19, wherein the water-immiscible medium is a water-immiscible fluid or a water-immiscible supercritical fluid.

22. A system as defined in claim 19, wherein the surfactant is sodium bi-(2-ethylhexyl)-sulfosuccinate and the molar ratio of water to surfactant is in the range from 21:1 to 31:1 inclusive.

23. A system as defined in claim 19, wherein the water-immiscible medium is a water-immiscible organic liquid and the amount of antibody or fragment in said system is up to and including 2 g per ml. of said organic liquid.

24. In a water-immiscible medium, a system for interacting a catalytic antibody or catalytic antibody fragment with a reactant, which comprises a plurality of microheterogeneously dispersed aqueous phase particles containing an amount of said catalytic antibody or catalytic antibody fragment sufficient to effect the interaction.

25. A system as defined in claim 24, wherein said microheterogeneous dispersion of aqueous phase particles is a microemulsion or a dispersion of aqueous reverse micelles, said aqueous phase contains a catalytic monoclonal antibody, and is adapted for the conversion of one or more reactants to one or more products.

26. A system as defined in claim 24, wherein the water-immiscible medium is a water-immiscible fluid or a water-immiscible supercritical fluid.

27. A system as defined in claim 24, wherein the surfactant is sodium bi-(2-ethylhexyl)-sulfosuccinate and the molar ratio of water to surfactant is in the range from 21:1 to 31:1 inclusive.

28. A system as defined in claim 24, wherein the water-immiscible medium in a water-immiscible organic liquid, and the amount of antibody or fragment in said system is up to and including 2 g per ml. of said organic liquid.

29. A system as defined in claim 10, 12, 19, 20, 24, or 26, wherein the antibody has a molecular weight of 150K daltons or greater.

30. A system as defined in claim 10, 13, 19, 20, 24 or 26, wherein the antibody is selected from the group consisting of IgM, 20-G9, 48-G7, IgA, IgD, IgE and IgG.

31. A system as defined in claim 9 or 18, wherein the ether is dioxane.

32. A method of interacting an antibody, or antibody fragment having functional capability, with at least one species, which comprises maintaining said antibody or fragment in a plurality of surfactant-stabilized microheterogeneously dispersed aqueous phase particles, said aqueous phase particles containing an amount of said antibody or fragment in a functional state sufficient to effect said interaction, at conditions under which the antibody or fragment is accessible to said species and that are sufficient to effect said interaction for a time sufficient for said interaction to occur; wherein said antibody or antibody fragment is catalytic in function.

33. A method as defined in claim 32, in which said species is an antigen, hapten, substrate or reactant.

34. A method as defined in claim 32, in which said surfactant is anionic, cationic, non-ionic, amphoteric or a combination of at least two of the foregoing.

35. A method as defined in claim 32, wherein said antibody is a monoclonal antibody.

36. A method of converting at least one reactant to at least one product, which comprises maintaining a system comprising a surfactant-stabilized microheterogeneous dispersion of aqueous phase, said aqueous phase containing an amount of catalytic antibody or catalytic antibody fragment sufficient to effect said conversion, at conditions under which the catalytic antibody or catalytic antibody fragment is accessible to said at least one reactant, and that are sufficient to effect the interaction between said catalytic antibody or catalytic antibody fragment and said at least one reactant to form said at least one product for a time sufficient for said interaction to occur.

37. A method as defined in claim 36, wherein the antibody is a monoclonal antibody.

38. A method as defined in claim 36, wherein said aqueous phase is a surfactant-stabilized microemulsion of aqueous phase particles, or a plurality of surfactant-stabilized reverse micelles.

39. A method as defined in claim 32, 35, 37, 38, wherein the antibody has a molecular weight of 150K daltons or greater.

40. A method as defined in claim 32, 35, 37, or 38, wherein the antibody is selected from the group consisting of IgM, 20-G9, 48-G7, IgA, IgD, IgE and IgG.

* * * * *